US00RE44521E

(19) United States
(12) Reissued Patent
Musho et al.

(10) Patent Number: US RE44,521 E
(45) **Date of Reissued Patent: *Oct. 8, 2013**

(54) ELECTROCHEMICAL-SENSOR DESIGN

(75) Inventors: Matthew K. Musho, York, PA (US); J. Oakey Noell, Nepean (CA); Andrew J. Edelbrock, Granger, IN (US); Dijia Huang, Granger, IN (US)

(73) Assignee: Bayer HealthCare LLC, Tarrytown, NY (US)

( * ) Notice: This patent is subject to a terminal disclaimer.

(21) Appl. No.: 12/257,031

(22) Filed: Oct. 23, 2008
(Under 37 CFR 1.47)

Related U.S. Patent Documents

Reissue of:
(64) Patent No.: 7,125,481
Issued: Oct. 24, 2006
Appl. No.: 10/864,011
Filed: Jun. 9, 2004

U.S. Applications:
(60) Division of application No. 09/861,437, filed on May 21, 2001, now Pat. No. 6,841,052, which is a continuation-in-part of application No. 09/731,943, filed on Dec. 8, 2000, now Pat. No. 6,531,040, which is a continuation-in-part of application No. 09/366,269, filed on Aug. 2, 1999, now abandoned.

(51) Int. Cl.
*G01N 27/327* (2006.01)

(52) U.S. Cl.
USPC ..... 205/775; 205/777.5; 205/778; 205/792; 204/403.01; 204/403.04; 204/416

(58) Field of Classification Search
USPC ..... 204/403.01–403.15; 205/777.5, 205/778, 792, 775
See application file for complete search history.

(56) References Cited

U.S. PATENT DOCUMENTS 4,172,770 A 10/1979 Semersky et al. ..... 204/1
4,549,952 A 10/1985 Columbus (Continued)

FOREIGN PATENT DOCUMENTS

CA 2419213 A1 6/2011
DE 19747875 A1 5/1999

(Continued)

OTHER PUBLICATIONS

European Search Report & Written Opinion corresponding to European Patent Application Serial No. 09010203.9, European Patent Office; dated Nov. 4, 2009; 7 pages.

(Continued)

*Primary Examiner* — Alex Noguerola
(74) *Attorney, Agent, or Firm* — Nixon Peabody LLP

(57) ABSTRACT

An electrochemical test sensor adapted to assist in determining the concentration of analyte in a fluid sample is disclosed. The sensor comprises a base that assists in forming an opening for introducing the fluid sample, a working electrode being coupled to the base, and a counter electrode being coupled to the base, the counter electrode and the working electrode being adapted to be in electrical communication with a detector of electrical current, and a sub-element being coupled to the base. A major portion of the counter electrode is located downstream relative to the opening and at least a portion of the working electrode. The sub-element is located upstream relative to the working electrode such that when electrical communication occurs between only the sub-element and the working electrode there is insufficient flow of electrical current through the detector to determine the concentration of the analyte in the fluid sample.

43 Claims, 1 Drawing Sheet

(56) References Cited

U.S. PATENT DOCUMENTS

| | | | | |
|---|---|---|---|---|
| 5,120,420 | A | 6/1992 | Nankai et al. | 204/403 |
| 5,141,868 | A | 8/1992 | Shanks et al. | 435/288 |
| 5,192,415 | A | 3/1993 | Yoshioka et al. | 204/403 |
| 5,264,103 | A | 11/1993 | Yoshioka et al. | 204/403 |
| 5,352,351 | A | 10/1994 | White et al. | 204/406 |
| 5,512,159 | A | 4/1996 | Yoshioka et al. | 204/403 |
| 5,575,403 | A | 11/1996 | Charlton et al. | 221/31 |
| 5,582,697 | A * | 12/1996 | Ikeda et al. | 205/777.5 |
| 5,620,579 | A | 4/1997 | Genshaw et al. | 204/402 |
| 5,628,890 | A | 5/1997 | Carter et al. | |
| 5,653,863 | A | 8/1997 | Genshaw et al. | 205/777.5 |
| 5,759,364 | A | 6/1998 | Charlton et al. | 204/403.14 |
| 5,786,584 | A * | 7/1998 | Button et al. | 235/462.15 |
| 5,798,031 | A | 8/1998 | Charlton et al. | 204/403 |
| 6,518,034 | B1 * | 2/2003 | Phillips et al. | 435/14 |
| 6,531,040 | B2 | 3/2003 | Musho et al. | |
| 6,814,844 | B2 | 11/2004 | Bhullar et al. | 204/403.01 |
| 6,841,052 | B2 | 1/2005 | Musho et al. | |
| 7,118,668 | B1 | 10/2006 | Edelbrock et al. | 205/777.5 |
| 7,122,110 | B2 | 10/2006 | Deng et al. | 205/777.5 |
| 7,125,481 | B2 | 10/2006 | Musho et al. | 205/775 |
| 2007/0045127 | A1 | 3/2007 | Huang et al. | 205/777.5 |

FOREIGN PATENT DOCUMENTS

| | | | |
|---|---|---|---|
| EP | 0 429 076 | A2 | 5/1991 |
| EP | 0 502 504 | A1 | 9/1992 |
| EP | 0537761 | | 4/1993 |
| EP | 0 636 879 | A2 | 2/1995 |
| EP | 0 679 720 | A1 | 11/1995 |
| EP | 0732406 | | 9/1996 |
| EP | 0732406 | A1 | 9/1996 |
| EP | 0735363 | | 10/1996 |
| EP | 0735363 | A1 | 10/1996 |
| EP | 0 795 601 | A2 | 9/1997 |
| EP | 0 795 748 | A1 | 9/1997 |
| EP | 0 800 080 | A2 | 10/1997 |
| EP | 0851224 | | 7/1998 |
| EP | 0 872 728 | A1 | 10/1998 |
| EP | 0 877 244 | A1 | 11/1998 |
| EP | 0 909 952 | A2 | 4/1999 |
| EP | 1 074 335 | A2 | 2/2001 |
| EP | 1 074 832 | A1 | 2/2001 |
| EP | 1 081 490 | A1 | 3/2001 |
| EP | 0851224 | B1 | 3/2002 |
| EP | 1 714 148 | B1 | 11/2011 |
| GB | 2 296 332 | A | 6/1996 |
| JP | 5-502727 | | 5/1993 |
| JP | 6109688 | | 4/1994 |
| JP | 1-932654 | | 5/1995 |
| JP | 8-502589 | | 3/1996 |
| JP | 08-304340 | | 11/1996 |
| JP | 8-320304 | | 12/1996 |
| JP | 9-222411 | | 8/1997 |
| JP | 10-318970 | | 12/1998 |
| JP | 2960265 | B2 | 10/1999 |
| JP | 2001-066279 | | 3/2001 |
| JP | 2003-004691 | | 1/2003 |
| JP | 2003-014684 | | 1/2003 |
| JP | 4814110 | | 9/2011 |
| WO | WO 99/60391 | | 11/1999 |

OTHER PUBLICATIONS

Extended European Search Report for European Application No. 10 18 3635 dated Dec. 23, 2010 (6 pages).

Notice of Opposition to European Patent EP 1 074 832 B1 dated Jun. 24, 2010, 30 pages.

Response to Opposition to European Patent EP 1 074 832 B1 filed with European Patent Office on Jan. 25, 2011, 12 pages.

Summons to Attend Oral Proceedings Pursuant to Rule 115(1) EPC to European Patent EP 1 074 832 B1 dated Sep. 3, 2012, 12 pages.

Letter from Opposer Concerning the Summons to Attend Oral Proceedings to Rule 115(1) EPC to European Patent EP 1 074 832 B1 dated Dec. 27, 2012, 48 pages.

Interlocutory decision in Oral Proceedings (Art. 101(3)(a) and 106(2) EPC) to European Patent EP 1 074 832 B1 dated Feb. 28, 2013, 42 pages.

* cited by examiner

ELECTROCHEMICAL-SENSOR DESIGN

Matter enclosed in heavy brackets [ ] appears in the original patent but forms no part of this reissue specification; matter printed in italics indicates the additions made by reissue.

This is a Divisional application of application Ser. No. 09/861,437 filed May 21, 2001, now U.S. Pat. No. 6,841,052 which in turn is a Continuation-In-Part of application Ser. No. 09/731,943 filed Dec. 8, 2000, now U.S. Pat. No. 6,531,040 B2, which is in turn a Continuation-In-Part of application Ser. No. 09/366,269, filed on Aug. 2, 1999, now abandoned.

BACKGROUND OF THE INVENTION

The present invention relates to an electrochemical biosensor that can be used for the quantitation of a specific component (analyte) in a liquid sample. Electrochemical biosensors of the type under consideration are disclosed in U.S. Pat. Nos. 5,120,420 and 5,264,103. These devices have an insulating base upon which carbon electrodes are printed with the electrodes being covered with a reagent layer comprising a hydrophilic polymer in combination with an oxidoreductase specific for the analyte. These patents typically involve a spacer element, a generally U shaped piece and a cover piece, so that when the base, spacer element and cover piece are laminated together, there is created a capillary space containing the electrodes covered by the reagent layer. In addition to the oxidoreductase, there is included an electron acceptor on the reagent layer or in another layer within the capillary space. A hydrophilic polymer, e.g. carboxymethylcellulose, is used to facilitate the drawing of the aqueous test fluid into the capillary space.

In U.S. Pat. No. 5,141,868 there is disclosed another sensor in which the electrodes are contained within a capillary space. This reference describes the method of preparing a sensor by mating the base and cover plates which are adhered to the base to form a capillary space into which a fluid test sample such as blood is drawn. An alternative to this design is disclosed in U.S. Pat. No. 5,798,031 in which the sensor is comprised of two pieces, a base and a concave lid which, when fused together, form the capillary space. In either embodiment, working and counter electrodes are screen printed onto the base so that an electrochemically created current can flow when these electrodes are electrically connected and a potential created between them.

These devices have a base plate and lid which are laminated together with the U shaped spacer element in between so that the U shaped portion is open to provide a capillary space between the base and the cover. Touching the opening in the side of the sensor to a drop of test fluid such as blood results in the blood being drawn into the capillary space, so that it covers the reaction layer on the surface of the working electrode. An enzymatic reaction between the oxidoreductase creates a flow of electrons which are carried by a mediator such as ferricyanide to the working electrode and flow through the working electrode to a meter which measures the magnitude of the current flow. The counter electrode serves several purposes. First, it provides a fixed potential against which the working electrode is controlled. Second, for a two electrode system, such as that depicted in FIGS. 1 and 2, the counter electrode is used to complete the electrical circuit. In this mode, each electron that is transferred to the working electrode is returned to the test solution on the counter electrode side. The device's software is programmed to correlate the magnitude of this flow with the concentration of analyte in the test sample. In order for this current to flow, a complete circuit is formed by covering both electrodes with the conductive test fluid and applying a potential therebetween.

A problem which is sometimes associated with this sort of sensor occurs when an insufficient amount of blood is applied to the opening so that the counter and working electrodes are not completely covered with the sample, resulting in an incomplete current flowing across the electrodes. Since the amount of analyte such as glucose detected by the sensor is directly portional to the current flowing through the detection meter, failure to completely cover the sensor's electrodes can result in an artificially low reading of the blood sample's analyte, e.g., glucose concentration. One technique for dealing with this under filling problem is disclosed in U.S. Pat. No. 5,628,890 which involves a mechanism for preventing any response from being detected when the sample volume is too low to provide an accurate reading. This device involves a strip comprising an elongated electrode support defining a sample transfer path for directional flow of the sample from a sample application point. There is placed a working electrode in the sample transfer path and a counter or reference electrode down stream from the working electrode in the sample transfer path. Failure of the blood sample to totally cover the working electrode will result in no response from the reading mechanism due to the absence of a closed circuit through which current can flow. Another technique for detecting short fills is disclosed in U.S. Pat. No. 5,582,697 where there is described a third electrode located downstream from the working and counter electrode, so that the circuit between the three electrodes will not be completed in the event of a short fill.

It would be desirable and it is an object of the present invention to provide an electrochemical sensor which affirmatively notifies the user when insufficient sample has contacted the electrodes. Upon receiving such a notice the user knows that an accurate reading cannot be obtained and that the sensor should be discarded in favor of a new one.

SUMMARY OF THE INVENTION

The present invention is an electrochemical sensor for detecting the concentration of an analyte, e.g. glucose, in a fluid test sample, such as blood. The sensor comprises:

1) a base which provides a flow path for the fluid test sample having on its surface a counter electrode and a working electrode in electrical communication with a detector of electrical current,
2) a reaction layer on the surface of at least the working electrode which contains an enzyme which reacts with the analyte to produce electrons that are transferred to the working electrode, and
3) a cover which when mated with the base member forms a capillary space with an opening for the introduction of fluid test sample into this space. The capillary space encloses the flow path for the fluid test sample in which the counter and working electrodes are contained. These electrodes are situated on the base in relation to the opening so that a major portion of the counter electrode is located downstream of the opening from the working electrode. The counter electrode contains a sub-element which is located upstream of the working electrode, so that when electrical communication between only the sub-element of the counter electrode and working electrode due to incomplete filling of the capillary space by the fluid test sample occurs, there is insufficient flow of electrical current through the detector to constitute a valid test for the concentration of analyte in the fluid test sample. In the event of such insufficient flow of electrical current, the detector gives an error signal to notify the user that the test has failed and that it should be repeated.

DESCRIPTION OF THE INVENTION

Figure 1:
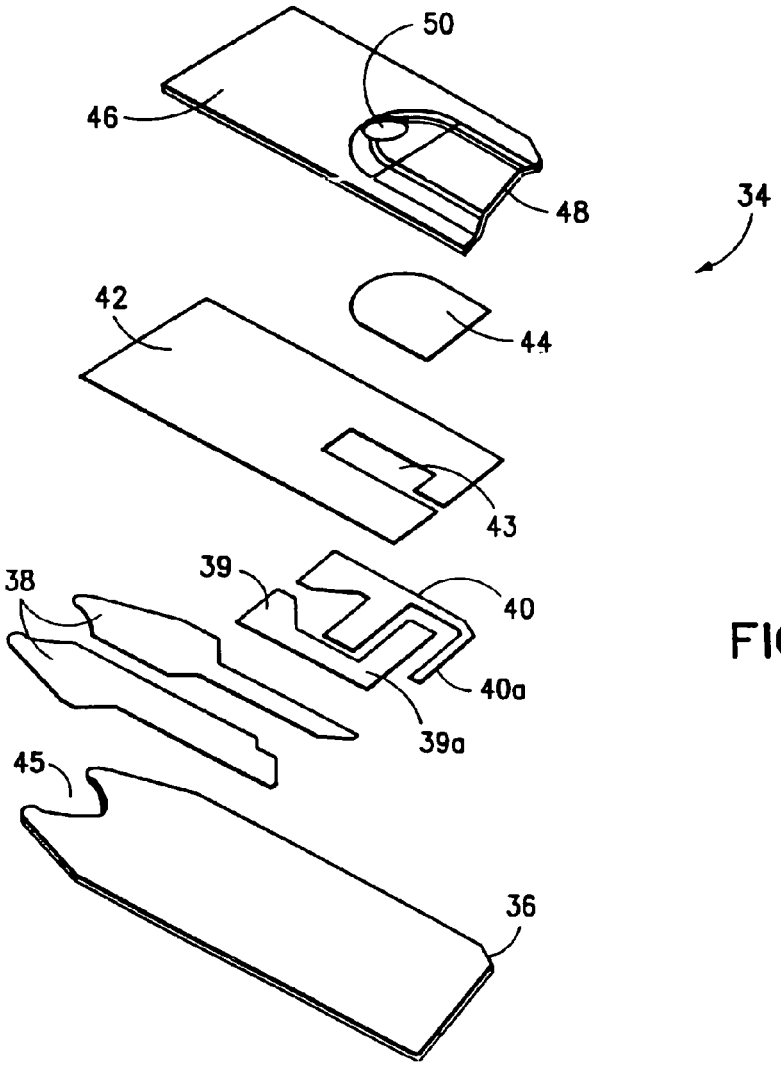
FIG. 1 represents an exploded view of the sensor of the present invention.

The construction of the electrochemical sensor with which the present invention is concerned is illustrated by FIG. 1. The sensor 34 is made up of insulating base 36 upon which is printed in sequence (typically by screen printing techniques) an electrical conductor pattern 38, an electrode pattern (39 and 40) an insulating (dielectric) pattern 42 and finally a reaction layer 44. The function of the reaction layer is to convert glucose, or another analyte in the fluid test sample, stoichiometrically into a chemical species which is electrochemically measurable, in terms of electrical current it produces, by the components of the electrode pattern. The reaction layer typically contains an enzyme which reacts with the analyte to produce mobile electrons on the electrode pattern and an electron acceptor such as a ferricyanide salt to carry the mobile electrons to the surface of the working electrode. The enzyme in the reaction layer can be combined with a hydrophilic polymer such as poly(ethylene oxide). The two parts 39 and 40 of the electrode print provide the working 39 and counter 40 electrodes necessary for the electrochemical determination of the analyte which is the crux of the present invention. The working and counter electrodes are configured in a manner such that the major portion of the counter electrode is located downstream (in terms of the direction of fluid flow along the flow path) from the exposed portion of the working electrode 39a. This configuration offers the advantage of allowing the test fluid to completely cover the exposed portion of the working electrode for all cases in which an undetected partial fill has occurred. However, sub-element 40a of the counter electrode is positioned upstream from working electrode upper element 39a so that when an inadequate amount of fluid (such as blood) to completely cover the working electrode enters the capillary space there will be formed an electrical connection between counter electrode sub-element 40a and exposed portion of the working electrode upper part 39a due to the conductivity of the blood sample. However, the area of the counter electrode which is available for contact by the blood sample is so small that only a very weak current can pass between the electrodes and hence through the current detector. By programming the current detector to give an error signal when any of the several error checking parameters is outside the tolerance range, the sensor device of the present invention actively advises the user that insufficient blood has entered the sensor's cavity and that another test should be conducted. The error checking parameters are derived from multiple current measurements. One main advantage of using error checking parameters, instead of directly checking a weak current is that the short-fill detection works at both high and low glucose levels. While the particular dimensions of the electrodes are not critical, the area of the sub-element of the counter electrode is typically less than about 10% than that of the working electrode and preferably less than about 6%. This element is made as small as possible in view of the restraints of the screen printing process. It is also contemplated that reaction layer 44 can be removed from contact with sub-element 40a of the counter electrode. This is accomplished by producing a screen that does not print reagent ink over the counter electrode sub-element 40b and serves the purpose of starving the sub-element for reagent thereby not allowing it to function as a proper counter electrode, so that an error condition is achieved in the case of failure of the test fluid to contact the bulk of the counter electrode 40. While sub-element 40a is depicted as being physically connected to, and therefore part of, the reference electrode 40, such physical connection is not critical. Such sub-element can be physically disconnected from the rest of the counter electrode provided that it is provided with its own connector and the sensor is equipped with a third contact to the detector.

The two parts 39 and 40 of the printed electrode provide the working and counter electrodes necessary for the electrochemical determination of analyte. The electrode ink, which is about 14μ (0.00055") thick, typically contains electrochemically active carbon. Components of the conductor ink are a mixture of carbon and silver which is chosen to provide a low chemical resistance path between the electrodes and the meter with which they are in operative connection via contact with the conductive pattern at the fish-tail end of the sensor 45. The counter electrode can be comprised of silver/silver chloride although carbon is preferred. The function of the dielectric pattern is to insulate the electrodes from the fluid test sample except in a defined area near the center of the electrode pattern to enhance the reproducibility of the meter reading. A defined area is important in this type of electrochemical determination because the measured current is dependent both on the concentration of the analyte and the area of the reaction layer which is exposed to the analyte containing test sample. A typical dielectric layer 42 comprises a UV cured acrylate modified polymethane which is about 10μ (0.0004") thick. The lid 46 which provides a concave space 48, and which is typically formed by embossing a flat sheet of deformable material, is punctured to provide air vent 50 and joined to the base 36 in a sealing operation. The lid and base can be sealed together by sonic welding in which the base and lid are first aligned and then pressed together between a vibratory heat sealing member or horn and a stationary jaw. The horn is shaped such that contact is made only with the flat, non-embossed regions of the lid. Ultrasonic energy from a crystal or other transducer is used to excite vibrations in the metal horn. This mechanical energy is dissipated as heat in the plastic joint allowing the bonding of the thermoplastic materials. The embossed lid and base can also be joined by use of an adhesive material on the underside of the lid. The method of joining the lid and base are more fully described in U.S. Pat. No. 5,798,031 which is incorporated herein by reference.

Suitable materials for the insulating base include polycarbonate, polyethylene terephthalate and dimensionally stable vinyl and acrylic polymers as well as polymer blends such as polycarbonate/polyethylene terephthalate and metal foil structures such as a nylon/aluminum/polyvinyl chloride laminate. The lid is typically fabricated from a deformable polymeric sheet material such as polycarbonate or an embossable grade of polyethylene terephthalate, glycol modified polyethylene terephthalate or a metal foil composition such as an aluminum foil structure. The dielectric layer can be fabricated from an acrylate modified polyurethane which is curable by UV light or moisture or a vinyl polymer which is heat curable.

The construction of a sensor according to the present invention is accomplished according to the following example:

EXAMPLE I

Figure 2:
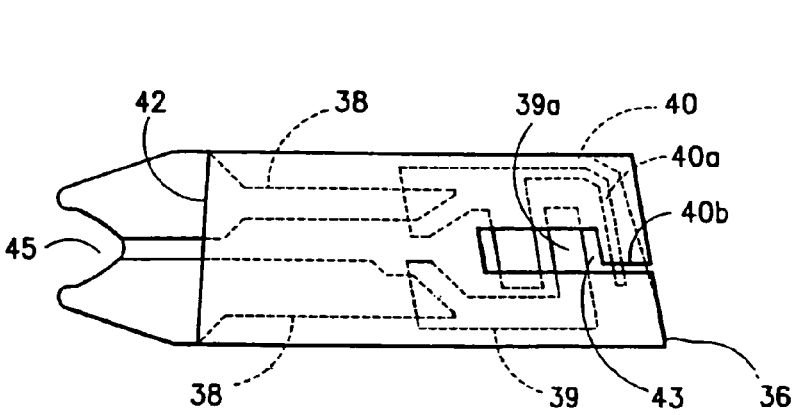
FIG. 2 represents the sensor's base and those elements of the sensor which are applied directly to the base.

The base stock, typically of polycarbonate, is printed with various inks to form the electrodes 39 and 40 and then overcoated with a dielectric layer 42 in a predetermined pattern designed to leave a desired surface of the electrode exposed to contact by the fluid test sample as it enters the space formed by the mating of lid 46 and base 36. The particular configuration of the dielectric layer 42 as depicted in FIG. 1 in which opening 43 leaves the reagent layer in electrical communication with the electrodes 39 and 40 is designed to define the extent to which all of the conductive elements (working, reference and sub-element electrodes) are exposed to the test fluid. Along with the printed conductive features, the dielectric layer defines the size of each of these elements. The electrodes are preferably printed so that the conductive and dielectric layers are close to 90 degrees to each other. This helps in the tolerance stackup for building the sensor because it reduces the registration issues since as either printing shifts around the element, definition remains constant. The sensor base of the present invention is also illustrated in FIG. 2 in which all elements on the base are shown in the same plane. The sensor's base 36 has conductive element 38 on its surface which is in turn overcoated with working electrode 39 and counter electrode 40. Dielectric layer 42 is not shown but instead the opening 43 in the dielectric layer is shown to illustrate the portions of working electrode 39 and counter electrode 40 which are exposed. The sub-element of the counter electrode which is in electrical communication with the larger portion of the counter electrode, designated as 40b, functions in this embodiment to provide an electrical conduction path with the working electrode such that the fluid can be detected as having reached the working electrode. Sufficient current will be provided to initiate the test sequence. If the test fluid fails to fill the sensor cavity and contact the major portion of the counter electrode, an error condition will be detected and communicated to the user of the device.

A large number of sensors according to the present invention are fabricated from a rolled sheet of polycarbonate which has been unrolled to provide a flat surface. This sheet is referred to as the lid stock since it serves as the source for a multiplicity of lids. There is typically placed a layer of thermoplastic adhesive on the underside of the lidstock after which concave areas 48 (FIG. 1) are embossed into the polycarbonate sheet and various holes are punched into the sheet to provide vent holes 50 and for registration and tracking before slit ribbons of lidstock are rolled up. The base stock, typically of polycarbonate, is printed with various inks to form the electrodes and then overcoated with the dielectric layer in a predetermined pattern designed to leave a desired surface of the electrode exposed to the reaction layer 44 when it is printed over the dielectric layer.

The present invention introduces the advantage of providing an electrochemical sensor in which the counter and working electrodes can be configured so that in the event of a short fill, the result will be affirmative as opposed to a neutral response, i.e. a failure of the detector to give any signal. Thus, when the amount of test fluid which enters the capillary space is sufficient to cover the sub-element of the counter electrode 40a, or 40b in the preferred embodiment, and that portion of the working electrode 39a which lies upstream from the main portion of the counter electrode 40, the detector will sense the values of error checking parameters derived from multiple current measurements exceeding their tolerance limits if the working electrode is not completely covered with the test fluid. The detector can be connected with the reading means to provide an error signal which will alert the user to the occurrence of a sort fill. The means of error checking are accomplished by algorithmically programming the meter to detect the short fill by measuring the current at a definite time period after the test fluid has electrically connected the sub-element of the counter electrode with the working electrode. The ratio of the currents for the measurements is used to determine if the sensor has filled properly. Thus, a short fill is determined by employing the following steps:

a) making multiple current measurements at different time periods when a driving potential is applied between the electrodes;
b) converting the multiple current measurements into error checking parameters; and
c) checking the values of the error checking parameters against their corresponding tolerance limits to determine if a short fill has occurred.

For example, in a sensor system which applied a 0.4 V potential for 10 seconds after a blood sample is applied (known as the burn-off period), opens the circuit (OV potential) for 10 seconds (known as the wait period) and then applies a 0.4 V potential during the 10 second read period; the steps are carried out as follows:

Referring to Step A in the above paragraph, three current measurements are made during the test sequence: 1) at the end of the burn-off period denoted as $I_{r10}$; 2) at the 5 second during the read period denoted as $I_{r5}$; and 3) at the end of the read period denoted as $I_{r10}$.

Then in Step B, two parameters are determined from the three current measurements. These two parameters are used to determine if the sensor's capillary space has filled properly. The first parameter is the Decay factor, which describes the shape of current time course. The second parameter is the Read-to-Burn ratio that characterizes the magnitude of initial current in relation to the final current. The decay factor, k, is defined as:

$$k = \frac{\ln(I_{r5}) - \ln(I_{r10})}{\ln(10) - \ln(5)} \qquad \text{Eq. 1}$$

Note: k characterizes how the current decays in a general current-glucose relationship $I=c\cdot G\cdot t^{-k}$, where I is the current, c is a constant, G is the glucose concentration, and t is the time.

The Read-to-Burn ratio, R/B is defined as:

$$R/B=I_{r10}/I_{b10} \qquad \text{Eq. 2}$$

In Step C, the values of these two parameters are checked against their tolerance limits to determine if a short fill occurred. The tolerance limits are not constant. They change as glucose level changes. The tolerance-limit checking is described as Conditions 1 and 2 below. The criteria for a short fill are either Condition 1 or Condition 2 is true.

Condition 1 (Decay factor checking):

$$\text{if } |k-(a_{k1}+b_{k1}\cdot G)|>w_k \text{ is true when } G\leq d_{k1}, \text{ or}$$

$$\text{if } |k-(a_{k2}+b_{k2}\cdot G)|>w_k \text{ is true when } d_{k1}<G\leq d_{k2}, \text{ or}$$

$$\text{if } |k-(a_{k3}+b_{k3}\cdot G)|>w_k \text{ is true when } G>d_{k2} \qquad \text{Eq. 3}$$

where $a_{k1}$, $a_{k2}$, $a_{k3}$, $b_{k1}$, $b_{k2}$, $b_{k3}$, $w_k$, $d_{k1}$, $d_{k2}$ and $d_{k3}$ are predetermined constants, G is the glucose measurement.

Condition 2 (R/B ratio checking):

$$\text{if } |R/B-(a_{c1}+b_{c1}\cdot G)|>w_c \text{ is true when } G\leq d_c, \text{ or}$$

$$\text{if } |R/B-(a_{c2}+b_{c2}\cdot G)|>w_c \text{ is true when } G>d_c \qquad \text{Eq. 4}$$

where $a_{c1}$, $a_{c2}$, $b_{c1}$, $b_{c2}$, $w_c$, and $d_c$ are predetermined constants, G is the glucose measurement.

The constants $a_k$'s, $b_k$'s, $d_k$'s and $w_k$ in Eq. 3 are predetermined experimentally:

Tests a large number of sensors at various glucose levels, G.

Calculates the decay factor, k, of each sensor from their $I_{b5}$ and $I_{b10}$ currents.

Plots all the data points in a k vs. G chart.

Fits a 3-piece piecewise-linear line to the data points in the k vs. G chart. These three pieces are $a_{k1}+b_{k1}\times G$ for $G\leq d_{k1}$; $a_{k2}+b_{k2}\times G$ for $G>d_{k1}$ and $\leq d_{k2}$; and $a_{k3}+b_{k3}\times G$ for $G>d_{k2}$ Add a tolerance width of $\pm w_k$ to the three lines so that the band between the $-w_k$ and $+w_k$ is wide enough to enclose all the normal data points in the chart.

The constants $a_c$'s, $b_c$'s, $d_c$ and $w_c$ in Eq. 4 are also predetermined experimentally in the same way, on a R/B vs. G chart.

A sample calculation is as follows:

Step A—Make three current measurements of a sensor: $I_{b10}$=505.1 nA, $I_{r5}$=656.5 nA, and $I_{r10}$=561.8 nA.

Step B—Determine the value of the decay factor k and R/B ratio:

The decay factor and read-to-burn ratio were calculated from the current measurements:

Decay factor $$k = \frac{\ln(I_{r5}) - \ln(I_{r10})}{\ln(10) - \ln(5)} = \frac{\ln(656.5) - \ln(561.8)}{\ln(10) - \ln(5)} = 0.225$$

Read-to-Burn ratio $$R/B=I_{r10}/I_{b10}=561.8/505.1=1.11$$

Step C—Check against the tolerance limits:

The constants used in this example were:

$a_{k1}$=0.36, $b_{k1}$=−0.0002 dL/mg, $w_k$=0.13, and $d_{k1}$=100 mg/dL

The glucose reading from the sensor system is 22.9 mg/dL.

Condition 1 was true because of the first line in Eq. 3 was true.

$$\text{if } |k-(a_{k1}+b_{k1}\cdot G)|>w_k \text{ is true when } G\leq d_{k1}$$

$$\Rightarrow$$

$$|0.225-(0.36-0.0002\cdot 22.9)|=0.1304>0.13 \text{ is true when } G=22.9\leq d_{k1}=100$$

No further check on Condition 2 was needed in this example, because Condition 1 was already true.

Therefore, this sensor was determined as a short fill.

The invention claimed is:

1. An electrochemical test sensor adapted to assist in determining the concentration of an analyte in a fluid test sample, the sensor comprising:

a base that assists in forming an opening for introducing the fluid test sample;

a working electrode *with an exposed portion not insulated from sample by dielectric material* being coupled to the base;

a counter electrode being coupled to the base, the counter electrode and the working electrode being adapted to be in electrical communication with a detector of electrical current; and a sub-element being coupled to the base, a major portion of the counter electrode being located downstream relative to the opening and [at least a] *the exposed* portion of the working electrode, the sub-element being located upstream relative to the working electrode such that [when electrical communication occurs between only the sub-element and the working electrode there is insufficient flow of electrical current through the detector to determine the concentration of the analyte in the fluid test sample] *a first current profile is produced in response to electrical communication between the sub-element and the working electrode, and a second current profile is produced in response to electrical communication between the sub-element, the major portion of the counter electrode, and the working electrode, the first current profile being indicative of a short fill.*

2. The sensor of claim 1 further comprising a cover adapted to be coupled to the base to form a capillary space, the capillary space having an opening for introducing the fluid test sample therein, the capillary space forming a flow path for the fluid test sample, the working electrode and the counter electrode being situated in the flow path.

3. The sensor of claim 2, wherein the cover includes an air vent.

4. The sensor of claim 1 further comprising a reaction layer located on the surface of at least the working electrode, the reaction layer comprising an enzyme adapted to react with the analyte to produce electrons, the electrons being adapted to be transferred to the working electrode.

5. The sensor of claim 1, wherein the area of the sub-element is less than 10% of the area of the working electrode.

6. The sensor of claim 1, wherein the sub-element and the counter electrode are physically connected.

7. A method of determining whether a sufficient quantity of a fluid test sample has been introduced to an electrochemical test sensor, the method comprising the acts of:

providing the electrochemical test sensor adapted to assist in determining the concentration of an analyte in a fluid test sample, the sensor comprising a base that assists in forming an opening for introducing the fluid test sample, a working electrode *with an exposed portion not insulated from sample by dielectric material* being coupled to the base, a counter electrode being coupled to the base, and a sub-element being coupled to the base, a major portion of the counter electrode being located downstream relative to the opening and [at least a] *the exposed* portion of the working electrode, the sub-element being located upstream relative to the working electrode;

introducing the fluid test sample to the test sensor; and determining whether a sufficient quantity of the fluid test sample has been introduced to the electrochemical test sensor and, if not, notifying a user that an insufficient quantity of the fluid test sample has been introduced.

8. The method of claim 7 further comprising, prior to the act of determining whether a sufficient quantity of the fluid test sample has been introduced to the electrochemical test sensor, measuring current at a plurality of time periods to obtain a plurality of current measurements.

9. The method of claim 8 further comprising providing a current to initiate a test sequence prior to the act of measuring current at a plurality of time periods.

10. The method of claim 8 further comprising, [prior to] *after* the act of measuring current at a plurality of time periods, the acts of:

converting the plurality of current measurements into a plurality of error checking parameters; and comparing the plurality of error checking parameters with their corresponding tolerance ranges.

11. The method of claim 10 wherein the act of notifying a user that an insufficient quantity of the fluid test sample has been introduced occurs when one or more of the plurality of error checking parameters are outside of their corresponding tolerance ranges.

12. The method of claim 11, wherein one or more of the plurality of error checking parameters is outside of its corresponding tolerance range when the fluid test sample fails to contact a major portion of the counter electrode.

13. The method of claim 10, wherein the plurality of error checking parameters is derived from the plurality of current measurements.

14. The method of claim 7, wherein the act of applying the fluid test sample to the sensor electrically connects the sub-element to the working electrode.

15. The method of claim 7, wherein the act of notifying a user that an insufficient quantity of the fluid test sample has been introduced includes providing an error signal.

16. The method of claim 7, wherein the test sensor further comprises a cover adapted to be coupled to the base to form a capillary space, the capillary space having an opening for introducing the fluid test sample therein, the capillary space forming a flow path for the fluid test sample, the working electrode and the counter electrode being situated in the flow path.

17. The method of claim 16, wherein the cover includes an air vent.

18. The method of claim 7, wherein the test sensor further comprises a reaction layer located on the surface of at least the working electrode, the reaction layer comprising an enzyme adapted to react with the analyte to produce electrons, the electrons being adapted to be transferred to the working electrode.

19. The method of claim 7, wherein the area of the sub-element is less than 10% of the area of the working electrode.

20. The method of claim 7, wherein the sub-element and the counter electrode are physically connected.

*21. An electrochemical test sensor adapted to assist in determining the concentration of an analyte in a fluid test sample, the sensor comprising:*

*a base that assists in forming an opening for introducing the fluid test sample;*

*a working electrode with an exposed portion not insulated from sample by dielectric material being coupled to the base;*

*a counter electrode being coupled to the base, the counter electrode and the working electrode being adapted to be in electrical communication with a detector of electrical current; and*

*a sub-element being coupled to the base, a portion of the counter electrode being located downstream relative to the opening and the exposed portion of the working electrode, the sub-element being located upstream relative to the working electrode such that a first current profile is produced in response to electrical communication between the sub-element and the working electrode, and a second current profile is produced in response to electrical communication between the sub-element, the portion of the counter electrode, and the working electrode, the first current profile being indicative of a short fill.*

*22. The sensor of claim 21 further comprising a cover adapted to be coupled to the base to form a capillary space, the capillary space having an opening for introducing the fluid test sample therein, the capillary space forming a flow path for the fluid test sample, the working electrode and the counter electrode being situated in the flow path.*

*23. The sensor of claim 22, wherein the cover includes an air vent.*

*24. The sensor of claim 21 further comprising a reaction layer located on the surface of at least the working electrode, the reaction layer comprising an enzyme adapted to react with the analyte to produce electrons, the electrons being adapted to be transferred to the working electrode.*

*25. The sensor of claim 21, wherein the area of the sub-element is less than 10% of the area of the working electrode.*

*26. The sensor of claim 21, wherein the sub-element and the counter electrode are physically connected.*

*27. The electrochemical test sensor of claim 21, further comprising a reaction layer including an enzyme adapted to react with the analyte to produce electrons, the electrons being adapted to be transferred to the working electrode, the reaction layer being in contact with at least a portion of the working electrode, the reaction layer being removed from contact with the sub-element.*

*28. A method of determining whether a sufficient quantity of a fluid test sample has been introduced to an electrochemical test sensor, the method comprising the acts of:*

*providing the electrochemical test sensor adapted to assist in determining the concentration of an analyte in a fluid test sample, the sensor comprising a base that assists in forming an opening for introducing the fluid test sample, a working electrode with an exposed portion not insulated from sample by dielectric material being coupled to the base, a counter electrode being coupled to the base, and a sub-element being coupled to the base, a portion of the counter electrode being located downstream relative to the opening and the exposed portion of the working electrode, the sub-element being located upstream relative to the working electrode;*

*introducing the fluid test sample to the test sensor; and*

*determining whether a sufficient quantity of the fluid test sample has been introduced to the electrochemical test sensor and, if not, notifying a user that an insufficient quantity of the fluid test sample has been introduced.*

*29. The method of claim 28 further comprising, prior to the act of determining whether a sufficient quantity of the fluid test sample has been introduced to the electrochemical test sensor, measuring current at a plurality of time periods to obtain a plurality of current measurements.*

*30. The method of claim 29 further comprising providing a current to initiate a test sequence prior to the act of measuring current at a plurality of time periods.*

*31. The method of claim 29 further comprising, after the act of measuring current at a plurality of time periods, the acts of:*

*converting the plurality of current measurements into a plurality of error checking parameters; and*

*comparing the plurality of error checking parameters with their corresponding tolerance ranges.*

*32. The method of claim 31 wherein the act of notifying a user that an insufficient quantity of the fluid test sample has been introduced occurs when one or more of the plurality of error checking parameters are outside of their corresponding tolerance ranges.*

*33. The method of claim 32, wherein one or more of the plurality of error checking parameters is outside of its corresponding tolerance range when the fluid test sample fails to contact the portion of the counter electrode.*

*34. The method of claim 31, wherein the plurality of error checking parameters is derived from the plurality of current measurements.*

*35. The method of claim 28, wherein the act of applying the fluid test sample to the sensor electrically connects the sub-element to the working electrode.*

*36. The method of claim 28, wherein the act of notifying a user that an insufficient quantity of the fluid test sample has been introduced includes providing an error signal.*

*37. The method of claim 28, wherein the test sensor further comprises a cover adapted to be coupled to the base to form a capillary space, the capillary space having an opening for introducing the fluid test sample therein, the capillary space forming a flow path for the fluid test sample, the working electrode and the counter electrode being situated in the flow path.*

*38. The method of claim 37, wherein the cover includes an air vent.*

*39. The method of claim 28, wherein the test sensor further comprises a reaction layer located on the surface of at least the working electrode, the reaction layer comprising an enzyme adapted to react with the analyte to produce electrons, the electrons being adapted to be transferred to the working electrode.*

*40. The method of claim 28, wherein the area of the sub-element is less than 10% of the area of the working electrode.*

*41. The method of claim 28, wherein the sub-element and the counter electrode are physically connected.*

*42. An electrochemical test sensor adapted to assist in determining the concentration of an analyte in a fluid test sample, the sensor comprising:*

*a base that assists in forming an opening for introducing the fluid test sample;*

*a working electrode with an exposed portion not insulated from sample by dielectric material being coupled to the base;*

*a counter electrode being coupled to the base, the counter electrode and the working electrode being adapted to be in electrical communication with a detector of electrical current;*

*a sub-element being coupled to the base, a portion of the counter electrode being located downstream relative to the opening and the exposed portion of the working electrode, the sub-element being located upstream relative to the working electrode; and*

*a reaction layer including an enzyme adapted to react with the analyte to produce electrons, the electrons being adapted to be transferred to the working electrode, the reaction layer being in contact with at least a portion of the working electrode, the reaction layer being removed from contact with the sub-element such that when electrical communication occurs between only the sub-element and the working electrode there is insufficient flow of electrical current through the detector to determine the concentration of the analyte in the fluid test sample.*

*43. The electrochemical test sensor of claim 42, wherein the area of the sub-element is less than 10% of the area of the working electrode.*

* * * * *

UNITED STATES PATENT AND TRADEMARK OFFICE

CERTIFICATE OF CORRECTION

PATENT NO. : RE44,521 E
APPLICATION NO. : 12/257031
DATED : October 8, 2013
INVENTOR(S) : Matthew K. Musho It is certified that error appears in the above-identified patent and that said Letters Patent is hereby corrected as shown below:

In the Specification

Add the following new paragraph before column 1, line 10 (i.e., before the first paragraph of the specification of U.S. Pat. No. RE44521):

-- NOTICE: More than one reissue application has been filed for the reissue of U.S. Patent No. 7,125,481. The reissue applications are application numbers 12/257,031 (the present application) and 14/022,189. In particular, application number 12/257,031 is a parent reissue application of Patent No. 7,125,481 and application number 14/022,189 is a continuation reissue of application number 12/257,031. --

Signed and Sealed this
Third Day of June, 2014

Michelle K. Lee

Michelle K. Lee
*Deputy Director of the United States Patent and Trademark Office*